United States Patent
Sweeney

(10) Patent No.: US 9,044,284 B2
(45) Date of Patent: Jun. 2, 2015

(54) INTERVERTEBRAL INSERT SYSTEM

(75) Inventor: Patrick J. Sweeney, Flossmoor, IL (US)

(73) Assignee: Spinal Generations, LLC, Mokena, IL (US)

( * ) Notice: Subject to any disclaimer, the term of this patent is extended or adjusted under 35 U.S.C. 154(b) by 402 days.

(21) Appl. No.: 12/893,986

(22) Filed: Sep. 29, 2010

(65) Prior Publication Data

US 2012/0078315 A1 Mar. 29, 2012

(51) Int. Cl.
| | |
|---|---|
| *A61B 17/58* | (2006.01) |
| *A61B 17/70* | (2006.01) |
| *A61B 17/88* | (2006.01) |
| *A61F 2/46* | (2006.01) |
| *A61F 2/44* | (2006.01) |

(Continued)

(52) U.S. Cl.
CPC ............... *A61B 17/8811* (2013.01); *A61F 2/44* (2013.01); *A61F 2/4455* (2013.01); *A61B 17/8819* (2013.01); *A61B 17/8825* (2013.01); *A61B 2017/00004* (2013.01); *A61F 2/442* (2013.01); *A61F 2/447* (2013.01); *A61F 2/4611* (2013.01); *A61F 2002/30062* (2013.01); *A61F 2002/30131* (2013.01); *A61F 2002/30166* (2013.01); *A61F 2002/30266* (2013.01); *A61F 2002/30538* (2013.01); *A61F 2002/30543* (2013.01); *A61F 2002/30736* (2013.01); *A61F 2002/30774* (2013.01); *A61F 2002/30777* (2013.01); *A61F 2002/30785* (2013.01); *A61F 2002/30827* (2013.01); *A61F 2002/30841* (2013.01); *A61F 2002/30904* (2013.01); *A61F 2002/4475* (2013.01); *A61F 2002/4627* (2013.01); *A61F 2002/4629* (2013.01); *A61F 2002/4631* (2013.01); *A61F 2002/4655* (2013.01); *A61F 2002/4692* (2013.01); *A61F 2310/00011* (2013.01); *A61F 2310/00017* (2013.01); *A61F 2310/00023* (2013.01); *A61F 2310/00029* (2013.01)

(58) Field of Classification Search
CPC ..................................................... A61F 2/4611
USPC ..................... 606/92–94, 99, 86 A, 246–249; 623/17.16
See application file for complete search history.

(56) References Cited

U.S. PATENT DOCUMENTS

| | | |
|---|---|---|
| 4,016,863 A | 4/1977 | Brantigan |
| 4,743,256 A | 5/1988 | Brantigan |

(Continued)

OTHER PUBLICATIONS

R90 Spacer Brochure, titled "Welcome to the New Revolution," R90 Spacer believed to be commercially available from Medtronic for more than one year prior to the filing date of the present application, 20 pages.

*Primary Examiner* — Nicholas Woodall
(74) *Attorney, Agent, or Firm* — Foley & Lardner LLP

(57) ABSTRACT

A system for delivering fluid to a space between two vertebrae is provided. The system includes a tool and an insert configured to be implanted in the space between two vertebrae. The tool includes a proximal end, a distal end and a structure at the distal end configured to be coupled to the insert. The tool further includes a first opening located near the proximal end of the tool, a second opening located near the distal end of the tool, and a passage extending between the first opening and the second opening. The first opening, the passage and the second opening provide a fluid delivery path from the proximal end to the exterior of the tool near the distal end. The second opening is positioned relative to the structure such that fluid is permitted to be delivered from the tool directly into the space between the two vertebrae.

15 Claims, 11 Drawing Sheets

(51) Int. Cl.
 *A61B 17/00* (2006.01)
 *A61F 2/30* (2006.01)

(56) References Cited

U.S. PATENT DOCUMENTS

| | | | |
|---|---|---|---|
| 4,834,757 A | 5/1989 | Brantigan | |
| 4,878,915 A | 11/1989 | Brantigan | |
| 5,015,247 A | 5/1991 | Michelson | |
| 5,192,327 A | 3/1993 | Brantigan | |
| 5,425,772 A | 6/1995 | Brantigan | |
| 5,609,636 A * | 3/1997 | Kohrs et al. | 623/17.16 |
| 5,645,598 A | 7/1997 | Brosnahan, III | |
| 5,665,122 A | 9/1997 | Kambin | |
| 5,766,253 A | 6/1998 | Brosnahan, III | |
| 5,865,847 A | 2/1999 | Kohrs et al. | |
| 5,968,098 A * | 10/1999 | Winslow | 623/17.11 |
| 6,080,158 A | 6/2000 | Lin | |
| 6,090,143 A | 7/2000 | Meriwether et al. | |
| 6,096,080 A | 8/2000 | Nicholson et al. | |
| 6,102,948 A | 8/2000 | Brosnahan, III | |
| 6,123,705 A | 9/2000 | Michelson | |
| 6,149,686 A | 11/2000 | Kuslich et al. | |
| 6,159,245 A | 12/2000 | Meriwether et al. | |
| 6,224,595 B1 | 5/2001 | Michelson | |
| 6,241,733 B1 | 6/2001 | Nicholson et al. | |
| 6,241,769 B1 | 6/2001 | Nicholson et al. | |
| 6,258,094 B1 | 7/2001 | Nicholson et al. | |
| 6,261,293 B1 | 7/2001 | Nicholson et al. | |
| 6,261,295 B1 | 7/2001 | Nicholson et al. | |
| 6,267,763 B1 | 7/2001 | Castro | |
| 6,290,724 B1 | 9/2001 | Marino | |
| 6,312,431 B1 | 11/2001 | Asfora | |
| 6,488,710 B2 | 12/2002 | Besselink | |
| 6,530,955 B2 | 3/2003 | Boyle et al. | |
| 6,576,016 B1 | 6/2003 | Hochshuler et al. | |
| 6,582,431 B1 | 6/2003 | Ray | |
| 6,679,887 B2 | 1/2004 | Nicholson et al. | |
| 6,743,255 B2 | 6/2004 | Ferree | |
| 6,800,093 B2 | 10/2004 | Nicholson et al. | |
| 6,805,697 B1 | 10/2004 | Helm et al. | |
| 6,827,743 B2 | 12/2004 | Eisermann et al. | |
| 6,942,697 B2 | 9/2005 | Lange et al. | |
| 7,320,686 B2 | 1/2008 | Serhan et al. | |
| 7,588,599 B2 | 9/2009 | Sweeney | |
| 7,655,010 B2 | 2/2010 | Serhan et al. | |
| 2002/0032483 A1 | 3/2002 | Nicholson et al. | |
| 2002/0123750 A1 | 9/2002 | Eisermann et al. | |
| 2003/0097136 A1 | 5/2003 | Hajianpour | |
| 2003/0153975 A1 | 8/2003 | Byrd, III et al. | |
| 2003/0232065 A1 | 12/2003 | Remington et al. | |
| 2003/0233147 A1 | 12/2003 | Nicholson et al. | |
| 2004/0006125 A1 | 1/2004 | Remington et al. | |
| 2004/0068268 A1* | 4/2004 | Boyd et al. | 606/92 |
| 2004/0186572 A1 | 9/2004 | Lange et al. | |
| 2004/0215202 A1 | 10/2004 | Preissman | |
| 2005/0038514 A1 | 2/2005 | Helm et al. | |
| 2005/0043733 A1 | 2/2005 | Eisermann et al. | |
| 2005/0070900 A1 | 3/2005 | Serhan et al. | |
| 2005/0107800 A1* | 5/2005 | Frankel et al. | 606/92 |
| 2005/0119747 A1 | 6/2005 | Fabris Monterumici et al. | |
| 2005/0246021 A1 | 11/2005 | Ringeisen et al. | |
| 2005/0273166 A1 | 12/2005 | Sweeney | |
| 2008/0154377 A1* | 6/2008 | Voellmicke | 623/17.16 |
| 2008/0172128 A1* | 7/2008 | Perez-Cruet et al. | 623/17.16 |
| 2009/0248164 A1 | 10/2009 | Sweeney | |

\* cited by examiner

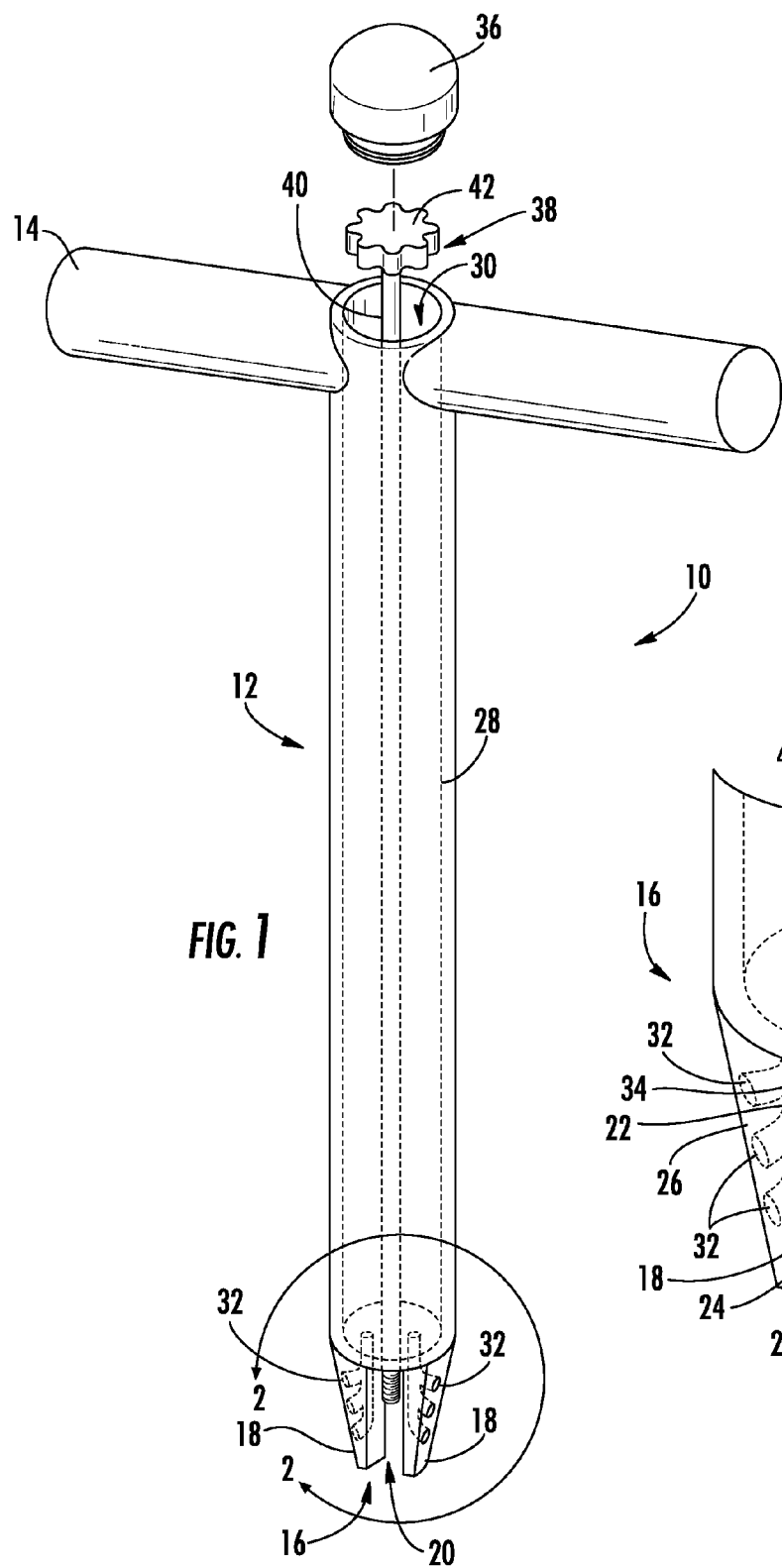
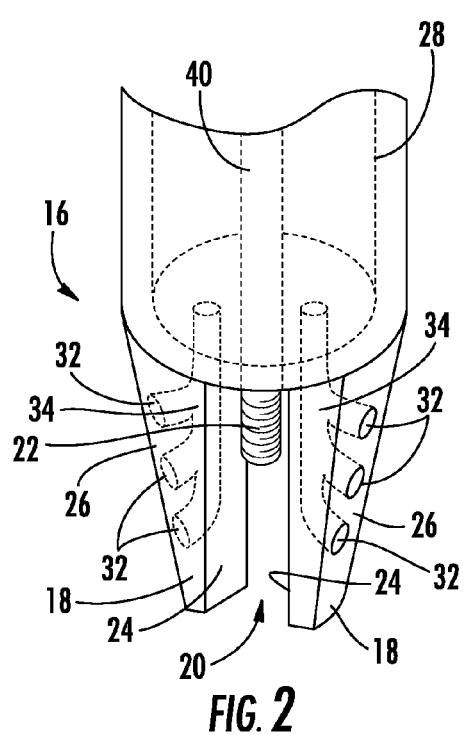
FIG. 1
FIG. 2

INTERVERTEBRAL INSERT SYSTEM

BACKGROUND OF THE INVENTION

The present invention relates generally to the field of orthopedic implants. The present invention relates specifically to an implantable intervertebral insert system, an insertion tool and related surgical methods for a spinal stabilization or spinal fusion procedure.

The spinal column includes twenty-six interlocking vertebrae. These vertebrae are separated by discs. The spine provides load-bearing support for one-half of the body's mass and it protects the nerves of the spinal column. The discs provide shock absorption and facilitate the bending of the spine. The combination of the vertebrae and discs at each vertebral segment allows for motion of the spine, in particular, flexing, rotation, and extension. The motion and support functions of the spine, in combination with the many interlocking parts and nerve roots associated with the spinal column, can result in back pain due to various reasons. Such back pain may result from the degeneration of discs due to age, disease, or injury. Further, vertebral bodies may be compromised due to disease or defect, such as a tumor, or injury, such as fracture. In the case of disc degeneration or other injury, the spacing between vertebrae may change and the curvature or shape of the spine may change resulting in a variety of problems including pain and reduced motion, flexibility, etc.

One or more intervertebral inserts may be placed into the space between adjacent vertebrae to reestablish the normal, healthy intervertebral spacing. In addition, a spinal fusion procedure may be performed to fuse together two or more adjacent vertebra. In a spinal fusion procedure, intervertebral inserts may be used in conjunction with bone graft material to facilitate the fusing together of the vertebral bodies adjacent to the inserts. In such spinal fusion procedures, the compromised disc may be removed, and one or more inserts may be placed into the intervertebral space to allow the formation of solid bone joining together the adjacent vertebrae. Creation of the desired intervertebral spacing and the desired spinal curvature at the location of the damaged disc tends to reduce pain and to improve spinal motion and flexibility.

SUMMARY OF THE INVENTION

One embodiment of the invention relates to a system for delivering fluid to a space between two vertebrae. The system includes a tool and an insert configured to be implanted in the space between two vertebrae. The tool includes a proximal end, a distal end and a structure at the distal end configured to be coupled to the insert. The tool further includes a first opening located near the proximal end of the tool, a second opening located near the distal end of the tool, and a passage extending between the first opening and the second opening. The first opening, the passage and the second opening provide a fluid delivery path from the proximal end to the exterior of the tool near the distal end. The second opening is positioned relative to the structure such that fluid is permitted to be delivered from the tool directly into the space between the two vertebrae.

Another embodiment of the invention relates to an intervertebral insert system including an insert configured to be implanted into an intervertebral space and a tool. The insert includes an outer surface, and the tool includes a proximal end and a distal end. The distal end has an inner surface and an outer surface, and the distal end is coupled to the insert. The inner surface of the distal end faces the outer surface of the insert and the outer surface of the distal end is configured to face the intervertebral space. The tool includes a first opening located near the proximal end and a second opening located along the outer surface of the distal end. A passage extends between the first opening and the second opening to provide a fluid delivery path from the proximal end to the exterior of the tool through the second opening.

Another embodiment of the invention relates to a tool for insertion of an intervertebral insert into an intervertebral space. The tool includes a shaft having a proximal end and a distal end, and the distal end of the shaft is configured to be coupled to the intervertebral insert. The tool includes a handle located at a proximal end of the shaft and a tapered section located at the distal end of the shaft. The tapered section extends toward the longitudinal axis of the shaft and away from the proximal end of the shaft. The tool includes a recess formed in the tapered section. The recess is configured to receive the intervertebral insert such that at least a portion of the intervertebral insert is located within the recess when the intervertebral insert is coupled to the shaft.

Alternative exemplary embodiments relate to other features and combinations of features as may be generally recited in the claims.

BRIEF DESCRIPTION OF THE DRAWINGS

This application will become more fully understood from the following detailed description, taken in conjunction with the accompanying figures, wherein like reference numerals refer to like elements in which:

FIG. 1 is a perspective view of an insertion tool, according to an exemplary embodiment;

FIG. 2 is an enlarged perspective view of the distal end section of the insertion tool of FIG. 1, according to an exemplary embodiment;

DETAILED DESCRIPTION

Before turning to the figures, which illustrate the exemplary embodiments in detail, it should be understood that the present application is not limited to the details or methodology set forth in the description or illustrated in the figures. It should also be understood that the terminology is for the purpose of description only and should not be regarded as limiting.

Referring generally to the figures, an intervertebral insert system is shown according to various exemplary embodiments. The system generally includes an implantable device (e.g., an insert, a spacer, a cage, etc.) that is inserted into a space between two vertebrae and an insertion tool to facilitate manipulation and implantation of the implantable device during a surgical procedure. The insertion tool is configured to allow for delivery of fluids to the intervertebral space during a surgical procedure, such as an insert implantation procedure, a spinal fusion procedure, etc.

Referring to FIGS. 1-8, in an exemplary embodiment, an intervertebral insert system includes an insertion tool 10 and an implantable device, shown as intervertebral spacer 50. Insertion tool 10 is configured to couple to or to engage with intervertebral spacer 50 to facilitate insertion and manipulation of the spacer 50 within the intervertebral space during a surgical procedure. Referring to FIG. 1 and FIG. 2, insertion tool 10 includes a body or shaft 12 and a handle 14 located at the proximal end of shaft 12. Handle 14 facilitates gripping of insertion tool 10 during use. Handle 14 is positioned substantially perpendicularly to the longitudinal axis of shaft 12. This orientation allows the user to grasp handle 14 and to rotate insertion tool 10 about its longitudinal axis.

Figure 3:
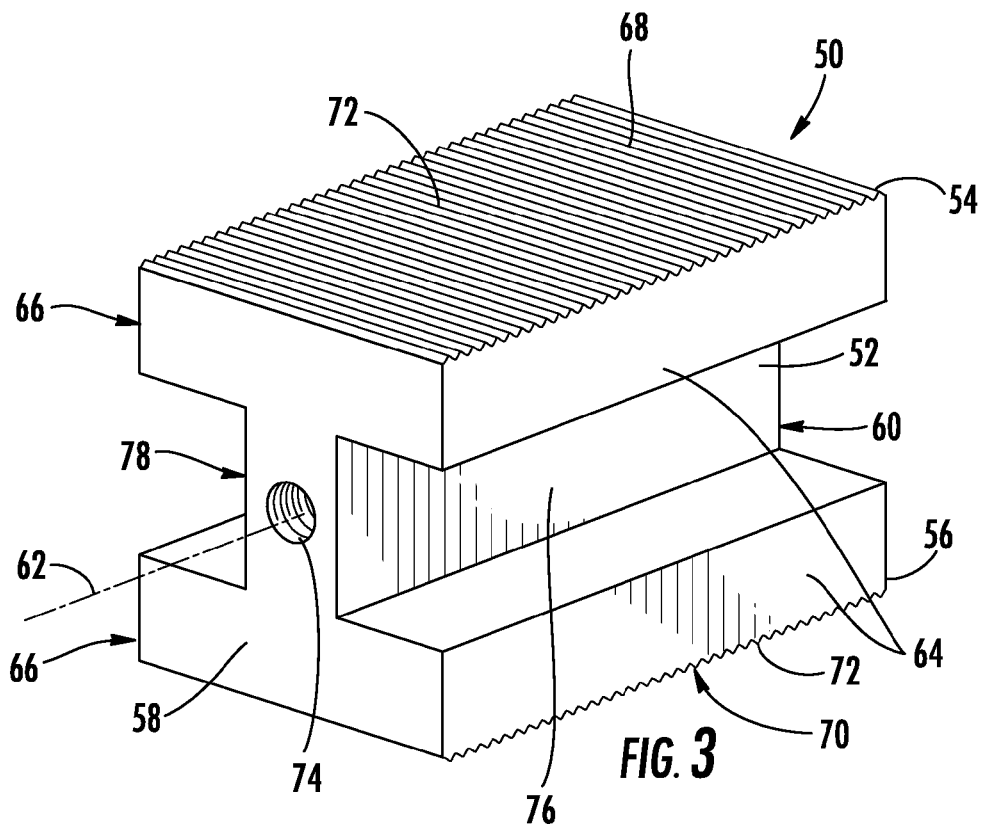
FIG. 3 is a perspective view of an intervertebral spacer, according to an exemplary embodiment.

Insertion tool 10 includes a distal end 16 of shaft 12 that is configured to be coupled to an implantable device or insert, such as intervertebral spacer 50, shown in FIG. 3. Distal end 16 includes an attachment mechanism or structure, shown as pair of arms 18, configured to be coupled to spacer 50 and a recess 20 located between arms 18. Recess 20 is configured to receive spacer 50 such that at least a portion of spacer 50 is located within recess 20. Arms 18 are configured to couple tool 10 to spacer 50 such that the position of spacer 50 is fixed relative to tool 10. This connection between tool 10 and spacer 50 allows the user to move, position, and rotate spacer 50 via interaction with tool 10.

In one embodiment, spacer 50 is coupled to tool 10 via a press-fit engagement between the inner surfaces 24 of arms 18 and the outer surfaces of spacer 50. Thus, in this embodiment, friction and compression between inner surfaces 24 of arms 18 and the outer surfaces of spacer 50 is sufficient to couple spacer 50 and tool 10 together without the use of any additional attachment mechanisms.

In the exemplary embodiment shown, insertion tool 10 also includes an additional attachment mechanism, shown as threaded post or screw 22 (see FIG. 2), located within recess 20 that extends in the direction of the longitudinal axis of shaft 12. Threaded post 22 is configured to engage a threaded aperture of spacer 50 to further facilitate coupling between tool 10 and spacer 50. In the embodiment shown in FIG. 1 and FIG. 2, the intervertebral insert system includes an attachment tool, shown as threaded tool 38, and threaded post 22 is the distal end of threaded tool 38. Threaded tool 38 includes a shaft 40 and a knurled handle 42 located at the proximal end of shaft 40. Shaft 40 of threaded tool 38 extends through cannulation 28 of tool 10 such that threaded post 22 engages the threaded aperture of spacer 50 to facilitate coupling of spacer 50 to tool 10. The user rotates threaded tool 38 via handle 42 such that threaded post 22 is threadably engaged with the threaded aperture of spacer 50.

In another embodiment, threaded post 22 may be a screw or other coupling device that is mounted to and that extends from tool 10. In one such embodiment, tool 10 may include a channel or opening that provides access to the threaded post 22 such that the user may employ a turning tool to rotate threaded post 22 such that the threaded post 22 is threadably engaged with the threaded aperture of spacer 50. In one such embodiment, the upper end or head of threaded post 22 may be located within cannulation 28 of tool 10 such that cannulation 28 provides access to threaded post 22. In this embodiment, tool 38 may be a turning tool such as an Allen wrench or screw driver that engages the head of post 22. In another embodiment, instead of threadably engaging the aperture of spacer 50, post 22 may not be threaded and may engage the aperture of spacer 50 via a snap-fit arrangement, a press-fit arrangement, etc. In another embodiment, the additional attachment mechanism may include a permanent magnet positioned within recess 20 or within arms 18 configured to be coupled magnetically to the material of spacer 50.

Arms 18 each have an outer surface 26. As shown in FIG. 1, outer surfaces 26 are angled inward toward the longitudinal axis of shaft 12. In this embodiment, outer surfaces 26 are tapered such that the distance between the two outer surfaces 26 decreases as the distance from the proximal end of tool 10 increases. The tapered outer surfaces 26 form a tapered section located at the distal end of the shaft of tool 10 that extends both away from the proximal end and toward the longitudinal axis of shaft 12. In this embodiment, recess 20 is formed in the tapered section of shaft 12 such that the inner surfaces 24 of arms 18 define the lateral walls of recess 20. This tapered configuration facilitates insertion of spacer 50 into the intervertebral space by providing gradual separation or distraction of adjacent vertebrae as the distal end 16 of tool 10 is inserted between two adjacent vertebra. In addition, outer surfaces 26 are substantial smooth allowing surfaces 26 to easily slide past the upper and lower faces of adjacent vertebrae during insertion to further facilitate insertion of spacer 50.

In the embodiment shown in FIG. 1, shaft 12 is substantially cylindrical in shape, and outer surfaces 26 of arms 18 are also curved to match the curvature of the outer surface of the cylindrical shaft 12. In other embodiments, shaft 12 and outer surfaces 26 may be other shapes. For example, in one embodiment, shaft 12 may be substantially cylindrical in shape and outer surfaces 26 may be substantially planar surfaces. In another embodiment, shaft 12 may have a wide variety of other cross-sectional shapes (e.g., oval, elliptical, square, rectangular, multi-faced, etc.).

As explained in more detail below regarding FIG. 7, insertion tool 10 is configured to provide a fluid delivery path from the proximal end to exterior of the tool near the distal end of shaft 12 such that fluid may be delivered directly to the intervertebral space. As indicated by broken lines in FIG. 1, insertion tool 10 includes an internal passage or channel, shown as cannulation 28, that extends from a proximal opening 30 to one or more openings 32 located through outer surfaces 26 of arms 18. Openings 32 are located at the distal ends of channels 34 (also shown in broken lines in FIG. 1), and channels 34 provide fluid communication from the central cannulation 28 to openings 32. In this arrangement, a fluid (e.g., medicine) may be introduced into cannulation 28 via proximal opening 30 which then flows through cannulation 28 and out of openings 32 into the vertebral space into which spacer 50 is being inserted.

In other embodiments, tool 10 may include other types of fluid delivery paths to openings 32. In one embodiment, tool 10 may include a separate, dedicated cannulation extending the length of shaft 12 for each arm 18. In another embodiment, each opening 32 or various groups of openings 32 may include a separate, dedicated cannulation extending the length of shaft 12. This embodiment may allow the user to selectively deliver different fluids through different openings 32 of tool 10. In another embodiment, tool 10 may include a tube or conduit running along the outer surface of shaft 12 that provides fluid communication to openings 32.

In one embodiment, insertion tool 10 may include a plurality of openings 32 located along each of the outer surfaces 26 of arms 18. The embodiment shown in FIG. 1 includes three openings 32 located along the outer surface 26 of each arm 18. However, in other embodiments, outer surfaces 26 of arms 18 may each include various numbers of openings 32. Further, openings 32 may be spaced or positioned in a pattern along outer surfaces 26 to provide fluid delivery to the intervertebral space in a manner suitable for a particular application (e.g., even distribution to the intervertebral space, targeted distribution to the intervertebral space, etc.). Further, insertion tool 10 may also include openings located along the non-tapered portion of shaft 12.

Insertion tool 10 includes a plug or cap 36 that may be coupled to proximal opening 30 of cannulation 28. During insertion, material (e.g., blood, other bodily fluids, bone, etc.) may enter the cannulation of tool 10 via openings 32, and cap 36 may prevent this material from exiting cannulation 28 via proximal opening 30. When fluid is to be delivered to the intervertebral space through tool 10, cap 36 may be removed to allow a fluid source to be connected to cannulation 28. In another embodiment, cap 36 may be permanently attached to tool 10 covering proximal opening 30 and may be made from a self-sealing material (such as, surgical silicone). In this embodiment, a fluid source may be placed into communication with cannulation 28 by piercing cap 36 with a needle connected to the fluid source, and, when the needle is removed, the material of cap 36 self seals, resealing proximal opening 30.

Referring to FIG. 3, an implantable device, shown as intervertebral spacer 50, is shown according to an exemplary embodiment. In the embodiment shown, spacer 50 is a solid spacer (i.e., one without a hollow interior cavity) and is formed from a single integral piece of material. Spacer 50 includes a central body portion 52, a first portion, shown as upper portion 54, and a second portion, shown as lower portion 56. Spacer 50 also includes a proximal face 58 and a distal face 60 (shown in FIG. 4) located opposite proximal face 58. Upper portion 54 extends from one end of body portion 52, and lower portion 56 extends from the other end of body portion 52. Both upper portion 54 and lower portion 56 are substantially perpendicular to body portion 52 such that a cross-section taken perpendicular to longitudinal axis 62 is substantially "I" shaped. In the embodiment shown, the cross-sectional shape of spacer 50 remains constant along the length of longitudinal axis 62 such that both proximal face 58 and distal face 60 are also substantially "I" shaped.

Spacer 50 includes a pair of opposing insertion surfaces and a pair of opposing gripping surfaces. In the embodiment shown in FIG. 3, the pair of opposing insertion surfaces includes a first pair of insertion surfaces 64 on one side of spacer 50 and a second pair of insertion surfaces 66 on the opposite side of spacer 50. In addition, the pair of opposing gripping surfaces includes a first gripping surface 68 on one side of spacer 50 and a second gripping surface 70 on the opposite side of spacer 50. As shown, the pair of insertion surfaces are substantially perpendicular to the pair of gripping surfaces. As explained in more detail below, during insertion into the intervertebral space, first pair of insertion surfaces 64 and second pair of insertion surfaces 66 contact the lower face of the superior vertebra and the upper face of the inferior vertebra, respectively. First pair of insertion surfaces 64 and second pair of insertion surfaces 66 are substantially smooth surfaces such that the surfaces are able to slide past the surfaces of the adjacent vertebrae with relative ease during the insertion process.

Following insertion into the intervertebral space, tool 10 is rotated about its longitudinal axis causing spacer 50 to rotate 90 degrees about its longitudinal axis to bring first gripping surface 68 into contact with the lower face of the superior vertebra and second gripping surface 70 into contact with the upper face of the inferior vertebra. First gripping surface 68 and second gripping surface 70 each include a projecting structure (e.g., teeth, points, spikes, claws, etc.), shown as ridges 72, that are configured to provide stability to spacer 50 by engaging the adjacent vertebra and preventing lateral movement of spacer 50 once it has been properly positioned.

Spacer 50 includes an aperture, shown as threaded aperture 74, formed in proximal face 58. Threaded aperture 74 receives threaded post 22 of insertion tool 10 to couple spacer 50 to tool 10 prior to insertion. Body 52 includes a pair of opposing outer surfaces, shown as outer surfaces 76 and 78, which are substantially parallel to insertion surfaces 64 and 66. Outer surfaces 76 and 78 face in the same directions as insertion surfaces 64 and 66, respectively. To facilitate coupling between spacer 50 and tool 10, inner surfaces 24 of arms 18 engage or grip outer surfaces 76 and 78 such that spacer 50 is held relative to tool 10. In the embodiment shown, spacer 50 is a solid insert formed from a solid, single piece of material, and, as such, threaded aperture 74 is not in communication with a hollow central cavity and is not part of the fluid flow path into the intervertebral space.

Figure 4:
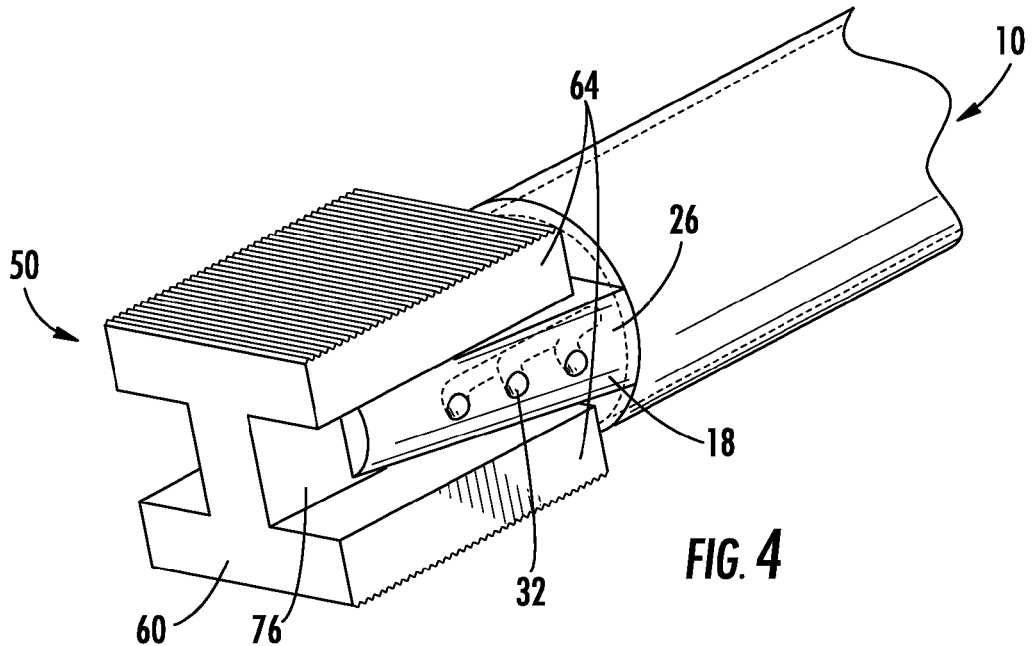
FIG. 4 is a perspective view of the intervertebral spacer of FIG. 3 coupled to the distal end section of the insertion tool of FIG. 1, according to an exemplary embodiment.

Referring to FIG. 4, insertion tool 10 is shown coupled to spacer 50. Spacer 50 is received within recess 20 between arms 18, and, in this arrangement, the inner surfaces of arms 18 face an outer surface (e.g., outer surfaces 76 and 78) of spacer 50 and the outer surfaces of arms 18 face the intervertebral space. With the "I" shaped embodiment of spacer 50, arms 18 are received in the recessed section formed between upper portion 54 and lower portion 56. As noted above, in this position, inner surfaces 24 of arms 18 engage outer surfaces 76 and 78 such that spacer 50 is coupled to tool 10. At least a portion of outer surfaces 26 of arms 18 extend above insertion surfaces 64 and 66, which allows these portions of outer surfaces 26 to engage the faces of the adjacent vertebral bodies during insertion.

Figure 5:
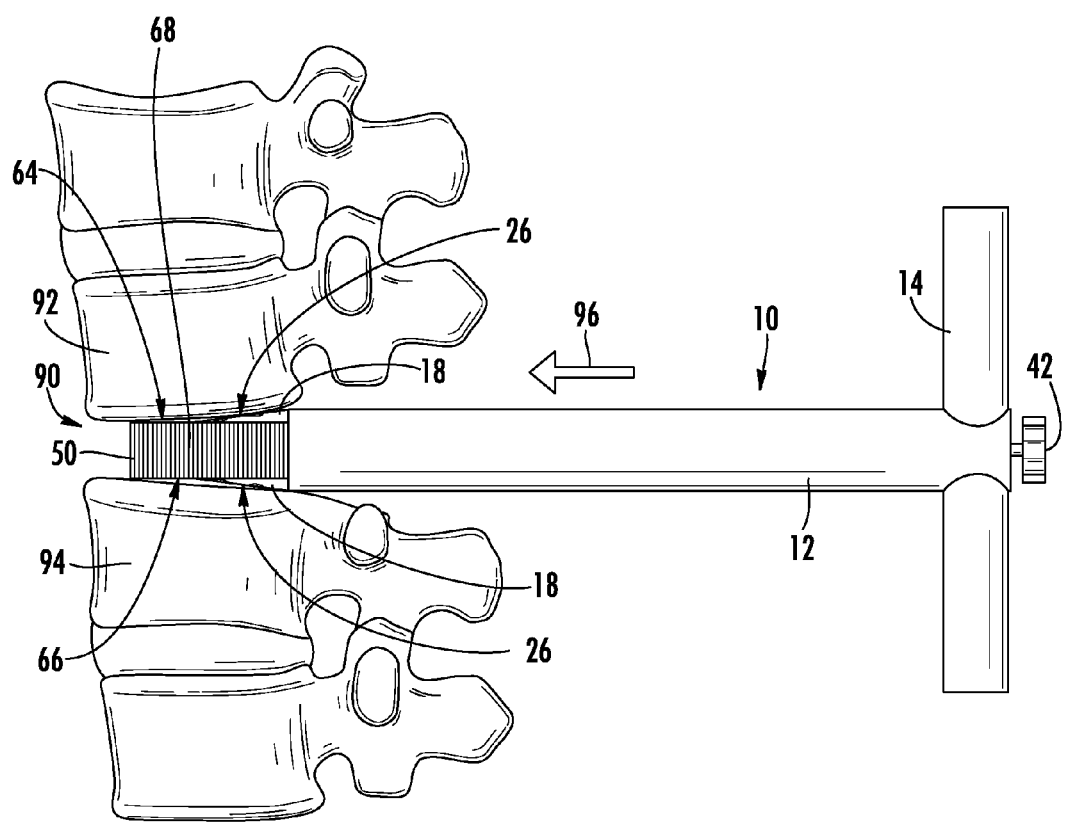
FIG. 5 is a side view of an intervertebral spacer coupled to an insertion tool, shown during insertion into the intervertebral space and prior to rotation, according to an exemplary embodiment.
Figure 6:
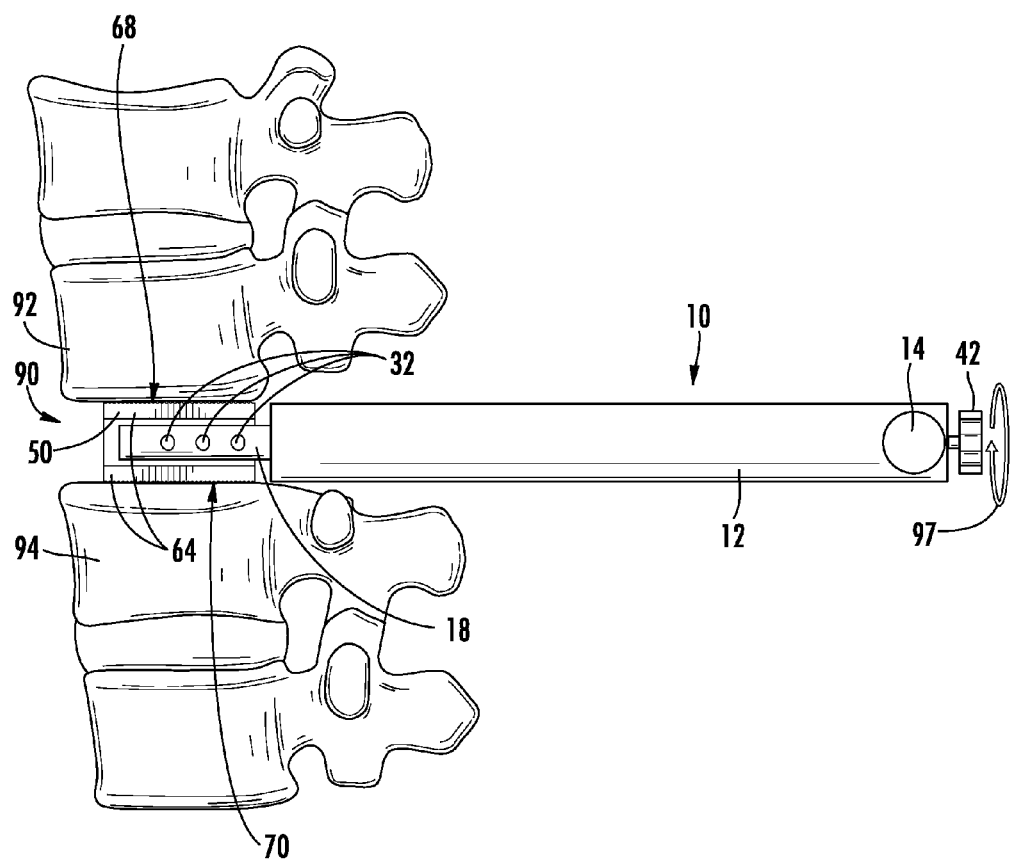
FIG. 6 is a side view of an intervertebral spacer coupled to an insertion tool, shown during insertion into the intervertebral space and following rotation, according to an exemplary embodiment.

Referring to FIG. 5 and FIG. 6, insertion of spacer 50 into a space between two vertebrae, shown as the intervertebral space 90 between superior vertebral body 92 and inferior vertebral body 94, is illustrated according to an exemplary embodiment. FIG. 5 shows spacer 50 in the insertion orientation. Prior to insertion of spacer 50, one or more images of the portion of the patient's spine may captured using an imaging system (e.g., x-ray, CT, MRI, etc.). The captured images may be used to select the proper type or configuration of spacer 50 that is appropriate for use in conjunction with the anatomy of a particular patient. An incision is made in the patient's back along the portion of the patient's spine to be treated. The spine and disc space are then exposed for treatment. The damaged portions of the disc and other material may be removed from the disc space. During some procedures, as much of the disc annulus (not shown) as possible is left in place within intervertebral space 90 to facilitate retention of bone graft material and any fluids delivered to intervertebral space 90. Bone graft material may then be inserted into a portion of intervertebral space 90, leaving sufficient room for the insertion of one or more spacers into intervertebral space 90. Following insertion of bone graft material, one or more spacers may be inserted into intervertebral space 90. During other procedures, bone graft material may be inserted after one or more spacers has been inserted into intervertebral space 90.

Referring to FIG. 5, to insert spacer 50, the user holds handle 14 of tool 10 and applies a force to move spacer 50 into the intervertebral space 90 anteriorly from the posterior side of the spine as indicated by arrow 96. As best seen in FIG. 7, spacer 50 may be inserted from the posterior direction offset to one side of the vertebral midline. In one embodiment, two spacers 50 may be inserted within intervertebral space 90, one on each side of the vertebral midline to provide sufficient support to the entire intervertebral space. In one such embodiment shown in FIG. 8, the two spacers 50 are situated substantially symmetrically about the vertebral midline within intervertebral space 90.

Referring to FIG. 5, spacer 50 is inserted such that first pair of insertion surfaces 64 contact the bone material of the lower face of the superior vertebral body 92 and second pair of insertion surfaces 66 contact the bone material of the upper face of the inferior vertebral body 94, respectively. Because first pair of insertion surfaces 64 and second pair of insertion surfaces 66 are substantially smooth, spacer 50 slides past superior vertebral body 92 and inferior vertebral body 94 as spacer is moved in the direction indicated by arrow 96.

FIG. 5 shows spacer 50 being inserted from the posterior direction. However, in other embodiments other surgical approaches may be used. For example, spacer 50 may be inserted from the posterolateral, lateral or anterior directions.

As shown in FIG. 5, a portion of outer surfaces 26 of arms 18 extend above and below insertion surfaces 64 and 66 of spacer 50 to contact the lower face of the superior vertebral body 92 and the upper face of the inferior vertebral body 94, respectively. The tapered shape of outer surfaces 26 of arms 18 causes distraction or separation of the adjacent vertebrae during insertion of spacer 50. The distraction provided by tapered outer surfaces 26 facilitates rotation of spacer 50 into its final position by providing the extra space needed between the vertebrae to receive spacer 50 in its final position. In particular, the distraction created by the tapered shape of outer surfaces 26 of arms 18 during insertion is sufficient to allow spacer 50 to be rotated into its final position without requiring additional distraction of the adjacent vertebrae prior to rotation. Further, the circumferential curve of outer surfaces 26 of the arms 18 facilitates sliding of arms 18 past the adjacent vertebrae during rotation of the insert into the final position.

Figure 8:
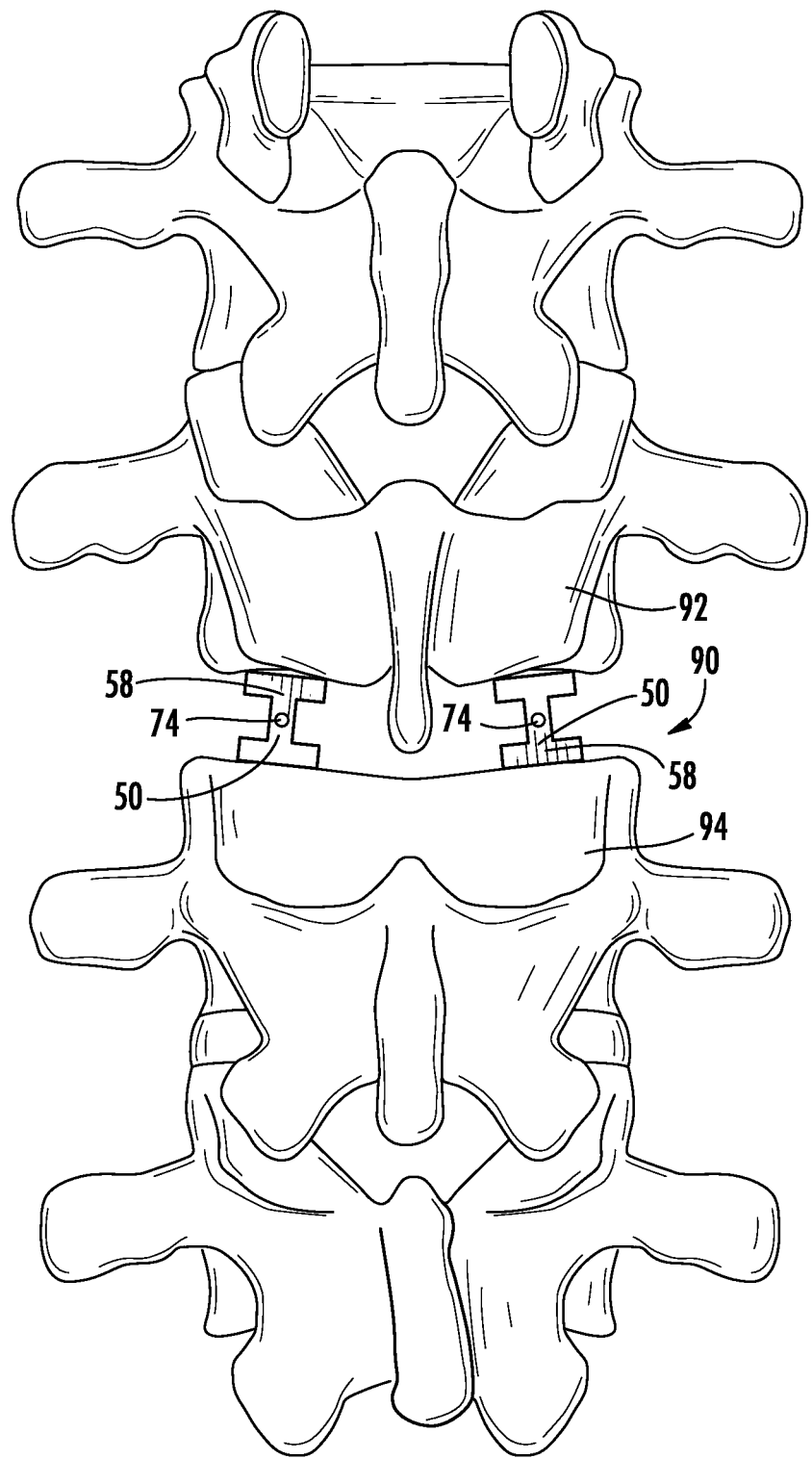
FIG. 8 is a rear side view showing a pair of intervertebral spacers positioned within the intervertebral space, according to an exemplary embodiment.

FIG. 6 and FIG. 8 show spacer 50 in the final position. Spacer 50 is rotated 90 degrees from the position shown in FIG. 5 to the position shown in FIG. 6 via application of rotational force to handle 14 of insertion tool 10 as indicated by arrow 97. As spacer 50 is rotated, upper gripping surfaces 68 and lower gripping surfaces 70 become engaged with the lower face of the superior vertebral body 92 and the upper face of the inferior vertebral body 94, respectively. As shown, ridges 72 engage the adjacent vertebrae resisting movement of spacer 50 once it has been implanted. In this orientation, spacer 50 helps to maintain the desired distance between superior vertebral body 92 and inferior vertebral body 94 and to place the spine into the desired shape and curvature. As shown in FIG. 8, two spacers 50, one on either side of the midline of the vertebrae, may be used to maintain appropriate separation of vertebral bodies 92 and 94. Once spacer 50 is properly positioned within intervertebral space 90, tool 10 is decoupled from spacer 50 leaving spacer 50 in place.

In this position, the lateral axis of body 52 is substantially parallel to the longitudinal axis of the spine (i.e., oriented substantially vertically), and the I-shaped configuration of spacer 50 effectively bears the loading of the spine (e.g., weight of the spine, forces generated by movement, etc.) such that the separation between the adjacent vertebrae is maintained. As used during a fusion procedure, spacer 50 acts to maintain the desired separation of the vertebral bodies during bone formation to help ensure that the superior vertebral body 92 and inferior vertebral body 94 are fused together at the appropriate distance from each other. It should be noted that the particular shape, dimensions and proportions of spacer 50 may be selected such that the spine maintains its curvature for the specific region (e.g., cervical, thoracic, lumbar, sacral and coccygeal) (the lumbar vertebrae are shown in FIGS. 5 and 6).

Figure 7:
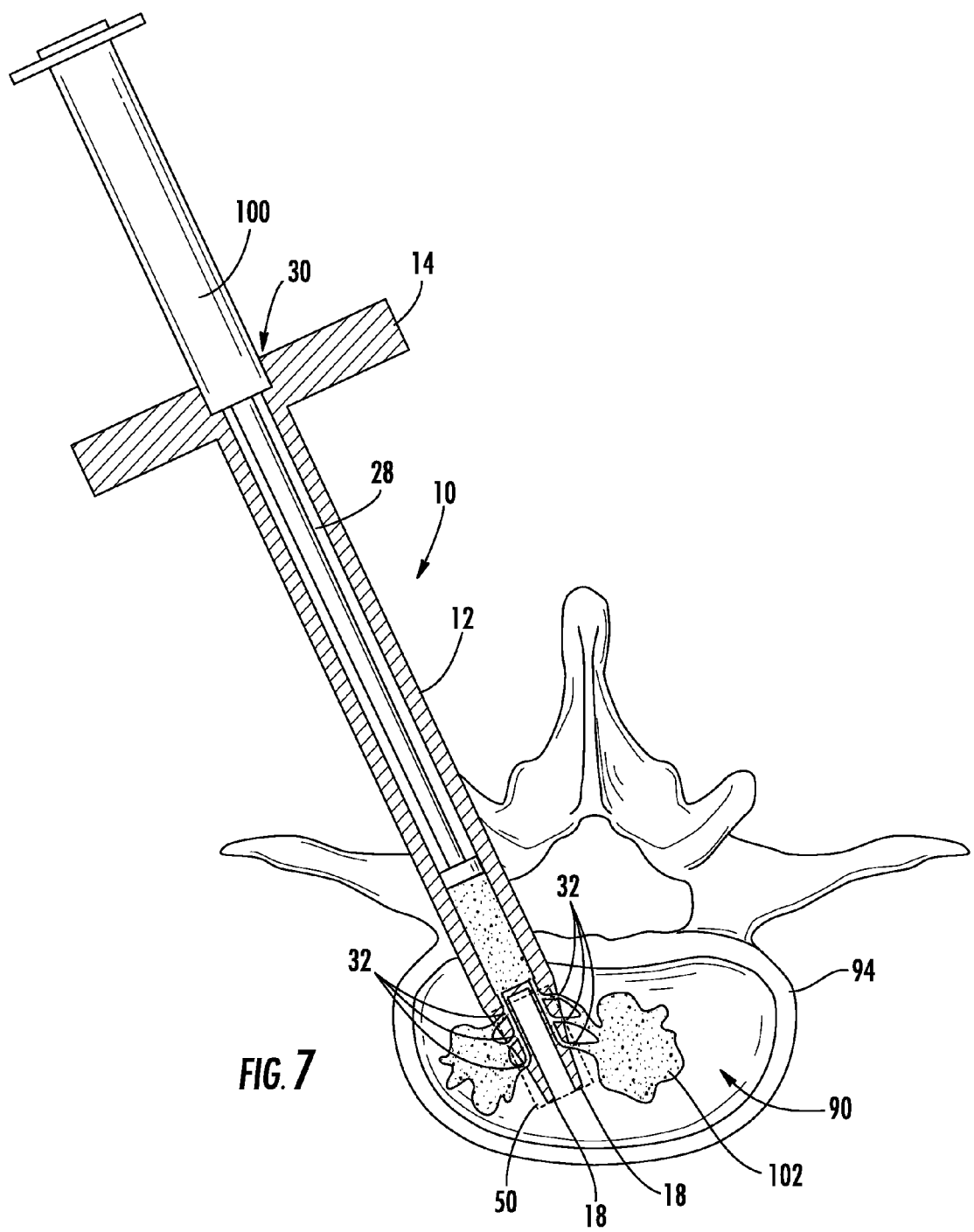
FIG. 7 is a top sectional view of an intervertebral spacer and insertion tool shown during delivery of a fluid into the intervertebral space, according to an exemplary embodiment.

Fluid delivery to intervertebral space 90 utilizing tool 10 is further depicted in FIG. 7. FIG. 7 is a top cross-sectional view showing tool 10 and spacer 50 located within intervertebral space 90 with upper portion 54 and lower portion 56 of spacer 50 shown in broken lines. Insertion tool 10 is configured to allow for fluid delivery directly into intervertebral space 90 without delivering fluid into or through spacer 50. Thus, in this embodiment, spacer 50 does not include any portion that forms part of the fluid delivery path into the intervertebral space. To deliver fluid to the intervertebral space 90, threaded tool 38 (shown in FIG. 1) is removed from cannulation 28 of tool 10, and a fluid source, shown as syringe 100, is coupled to cannulation 28 of shaft 12 via proximal opening 30. Generally, the fluid source typically includes a reservoir for holding an amount of fluid and a pressure source to pump the fluid from the reservoir, through cannulation 28 of tool 10, and out of openings 32 into intervertebral space 90. While the fluid source is shown in FIG. 7 as syringe 100, in other embodiments, the fluid source may be a pump (e.g., an infusion pump) or a bag (similar to an IV bag) coupled to tool 10 via tubing.

As shown in FIG. 6 and FIG. 7, arms 18 of tool 10 are engaged along outwardly facing surfaces (e.g., outer surfaces 76 and 78 of body 52) of spacer 50 such that openings 32 are in direct communication with intervertebral space 90. As shown in FIG. 7, with syringe 100 coupled to tool 10, fluid 102 may be forced through cannulation 28 and into the intervertebral space 90. Because arms 18 are positioned along either side of spacer 50, tool 10 provides a fluid delivery pathway directly to intervertebral space 90 on both sides of spacer 50.

In some embodiments, tool 10 may be configured to selectably deliver fluid to one side of spacer 50, instead of to both sides as shown in FIG. 7. In one such embodiment, one of the arms 18 includes openings 32, and the other arm 18 of tool 10 may be made from a solid piece of material without openings 32. The user may couple spacer 50 to tool 10 such that the arm 18 with openings 32 is located on the side of spacer 50 to which fluid is to be delivered. In another embodiment, the user may close or cap one or more openings 32 of arms 18 to selectably deliver fluid to the intervertebral space in the desired manner.

In some current intervertebral insert systems, fluid may be delivered through an insertion tool into a hollow cavity of a spacer or cage, and, in these systems, the fluid must then flow out of the hollow cavity of the spacer in order to reach the intervertebral space. In contrast to these systems, openings 32 positioned along the outer surfaces of arms 18 allow fluid to be delivered through tool 10 directly to the intervertebral space without requiring the fluid to be delivered first into the central cavity of a hollow spacer. In this arrangement, fluid is allowed to flow from openings 32 into the intervertebral space and then into contact with the outer surfaces of the spacer without requiring fluid to be delivered first into the intervertebral spacer. This configuration allows insertion tool 10 to be used with a solid intervertebral insert (i.e., one without a hollow cavity). Because a solid intervertebral insert may provide greater structural integrity than a hollow insert, insertion tool 10 and a solid insert (such as spacer 50) may be desirable in an application requiring a high strength insert. Further, because fluid delivery to the intervertebral space occurs directly through openings 32, insertion tool 10 provides for consistent and predictable fluid delivery characteristics that are not dependent on the structure or shape of the particular intervertebral spacer that is used with tool 10. Thus, tool 10 may be used with a variety of different intervertebral spacer designs and shapes while maintaining the desired fluid delivery characteristics determined by the number and arrangement of openings 32. Further, because tool 10 provides for direct fluid delivery to the intervertebral space on both sides of the spacer, tool 10 may provide for more complete delivery of fluid to intervertebral space 90 than if fluid were delivered first into a hollow spacer or were delivered to only one side of the spacer.

In one embodiment, syringe 100 may be operated as a suction device to remove or withdraw material from intervertebral space 90. In this embodiment, suction or a vacuum may be applied to cannulation 28 of tool 10 to draw material into cannulation 28 of tool 10 through openings 32. Once within cannulation 28, the withdrawn material may travel through cannulation 28 and out of proximal opening 30 where the material may be captured for a variety of uses. For example, bone or blood samples may be withdrawn from intervertebral space 90 for diagnostic testing in this manner.

Figure 9:
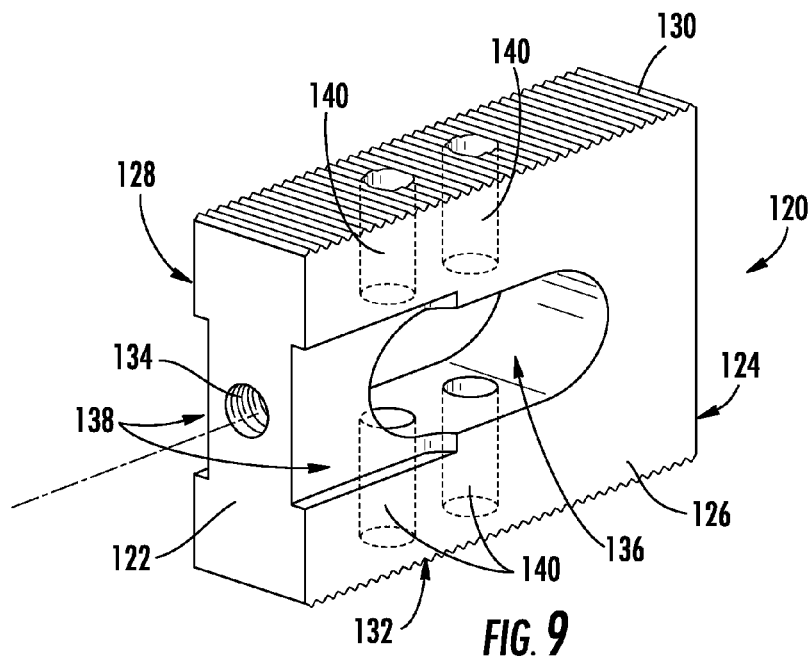
FIG. 9 is a perspective view of an intervertebral spacer, according to another exemplary embodiment.

Referring to FIG. 9, a second implantable device, shown as intervertebral spacer 120, is depicted according to an exemplary embodiment. Intervertebral spacer 120 is generally shaped as a rectangular prism. Intervertebral spacer 120 includes a proximal face 122, a distal face 124, a first insertion surface 126, a second insertion surface 128, a first gripping surface 130 and a second gripping surface 132. Intervertebral spacer 120 includes a threaded aperture 134 located along proximal face 122. Insertion surfaces 126 and 128, gripping surfaces 130 and 132 and threaded aperture 134 function substantially the same as discussed above regarding spacer 50.

Figure 10:
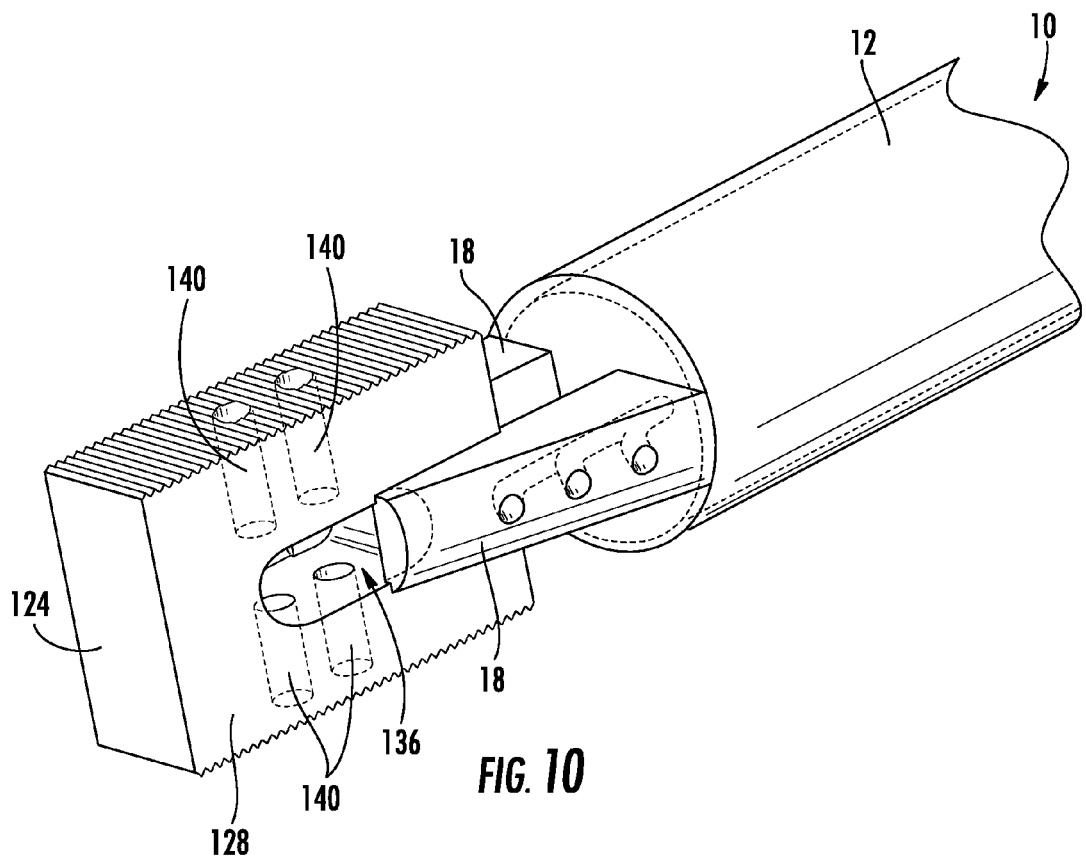
FIG. 10 is a perspective view of the intervertebral spacer of FIG. 9 coupled to the distal end section of the insertion tool of FIG. 1, according to an exemplary embodiment.

Spacer 120 includes a hollow central portion 136 and a depression 138 formed in each of the insertion surfaces 126 and 128. FIG. 10 shows spacer 120 coupled to insertion tool 10. As shown, arms 18 of tool 10 engage spacer 120 within depressions 138. Arms 18 of tool 10 only engage spacer 120 along a portion of its length such that hollow central portion 136 is exposed to or is in communication with the intervertebral space during insertion. For example, as shown, arms 18 do not substantially cover or block hollow central portion 136. This arrangement allows fluid that is delivered directly into the intervertebral space from tool 10 to flow from the intervertebral space into hollow central portion 136. This arrangement may also allow for bone in-growth into spacer 120 during a fusion procedure. Spacer 120 also includes a plurality of channels 140 extending from gripping surfaces 130 and 132 to hollow central portion 136. Channels 140 place gripping surfaces 130 and 132 in fluid communication with hollow central portion 136 such that fluid delivered into the intervertebral space is allowed to flow through channels 140 to the interface between the vertebral bone and gripping surfaces 130 and 132. Channels 140 may also allow for additional bone in-growth into spacer 120 further facilitating a fusion procedure.

Like spacer 50, spacer 120 is configured to be inserted into the intervertebral space in a first orientation in which insertion surfaces 126 and 128 contact the faces of the vertebrae adjacent the intervertebral space. The tapered end section of tool 10 provides for initial distraction of the adjacent vertebrae, and, when spacer 120 is at the desired position relative to the adjacent vertebrae, spacer 120 is then rotated, bringing gripping surfaces 130 and 132 into contact with the adjacent vertebrae.

Figure 11:
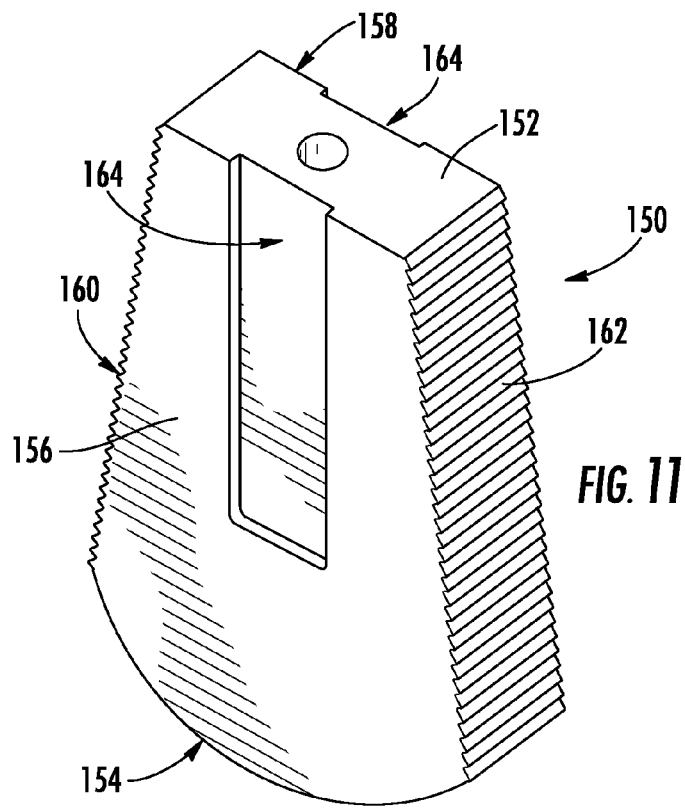
FIG. 11 is a perspective view of an intervertebral spacer, according to another exemplary embodiment.
Figure 12:
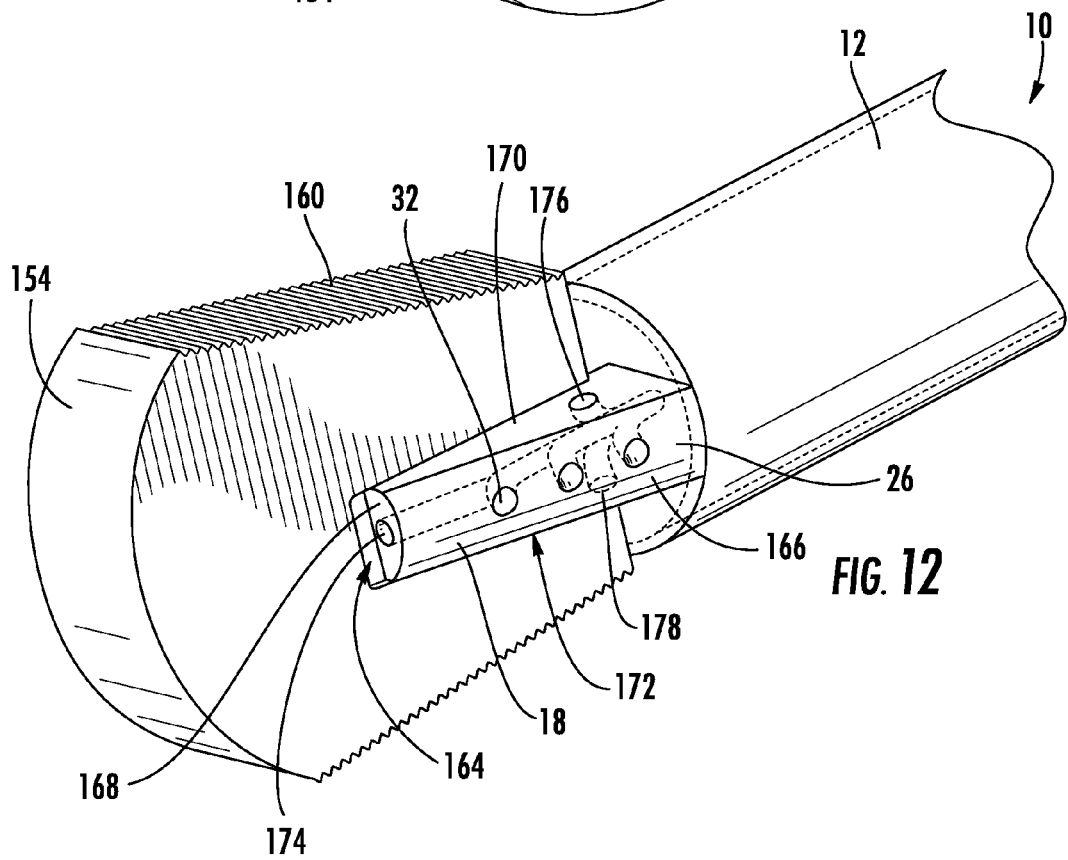
FIG. 12 is a perspective view of the intervertebral spacer of FIG. 11 coupled to the distal end section of the insertion tool of FIG. 1, according to an exemplary embodiment.

Referring to FIG. 11, a third implantable device, shown as intervertebral spacer 150, is shown according to an exemplary embodiment. Intervertebral spacer 150 includes a proximal face 152, a distal face 154, a first insertion surface 156, a second insertion surface 158 (opposite first insertion surface 156), a first gripping surface 160 and a second gripping surface 162. In this embodiment, distal face 154 is a convex curved surface. Spacer 150 includes recesses 164 formed in each of the insertion surfaces 156 and 158, and as shown in FIG. 12, arms 18 of tool 10 are received within recesses 164 when spacer 150 is coupled to tool 10. Insertion surfaces 156, 158, and gripping surfaces 160, 162 function substantially the same as discussed above regarding spacer 50.

Referring to FIG. 12, an exemplary embodiment of tool 10 with arms 18 coupled to spacer 150 is shown. Outer surface 26 of arm 18 includes a lateral surface 166, a distal surface 168, an upper surface 170 and a lower surface 172. Tool 10 may include one or more openings located along one or more of the surfaces of outer surface 26. Openings 32 are located along the lateral surface 166. In the embodiment shown, tool 10 may also include an opening 174 located on distal surface 168, an opening 176 located on upper surface 170 and an opening 178 located on lower surface 172. Like openings 32, openings 174, 176 and 178 are in fluid communication with cannulation 28 of tool 10 to allow for fluid delivery to the intervertebral space through distal surface 168, upper surface 170, and lower surface 172, respectively.

Figure 13:
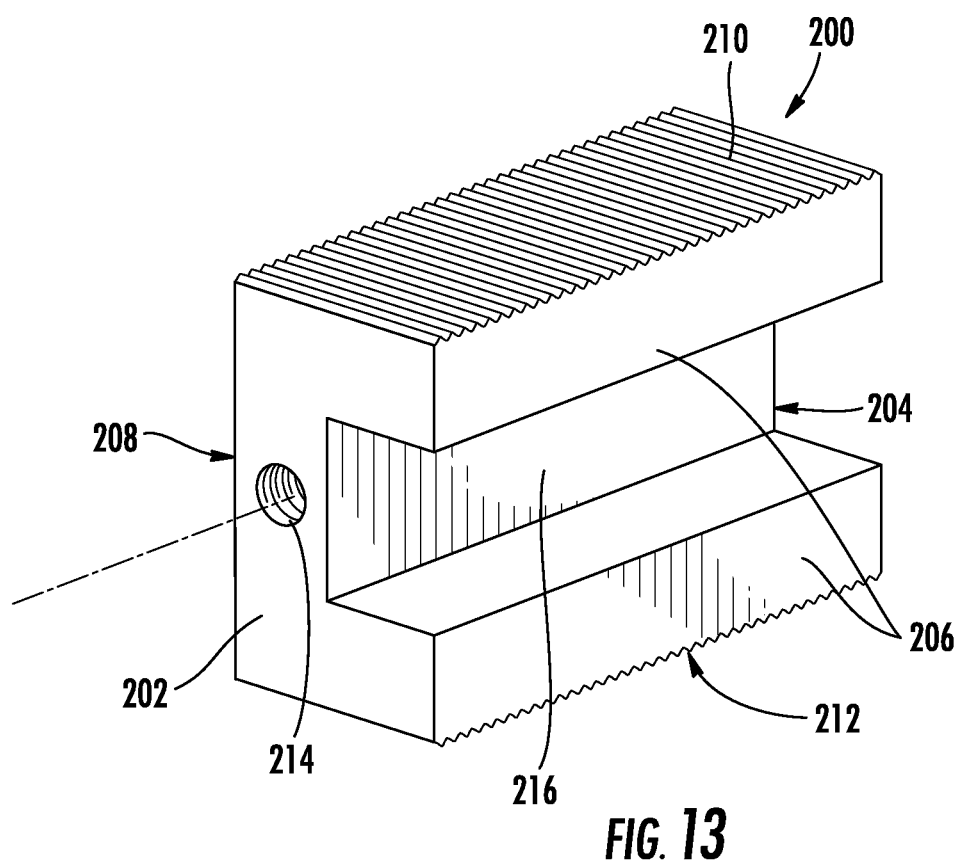
FIG. 13 is a perspective view of an intervertebral spacer, according to another exemplary embodiment.

Referring to FIG. 13, a fourth implantable device, shown as intervertebral spacer 200, is shown according to an exemplary embodiment. Intervertebral spacer 200 includes a proximal face 202, a distal face 204, a pair of insertion surfaces 206, an opposing insertion surface 208 (opposite pair of insertion surfaces 206), a first gripping surface 210 and a second gripping surface 212. Proximal face 202 includes a threaded aperture 214 that receives threaded post 22 to couple spacer 200 to tool 10. Spacer 200 includes a recessed, outer surface, shown as outer surface 216, which is substantially parallel to and recessed below pair of insertion surfaces 206. As can be seen, spacer 200 is substantially "C" shaped having a body portion and upper and lower portions positioned perpendicularly to the body portion. Insertion surfaces 206, 208 and gripping surfaces 210, 212 function substantially the same as discussed above regarding spacer 50.

Figure 14A:
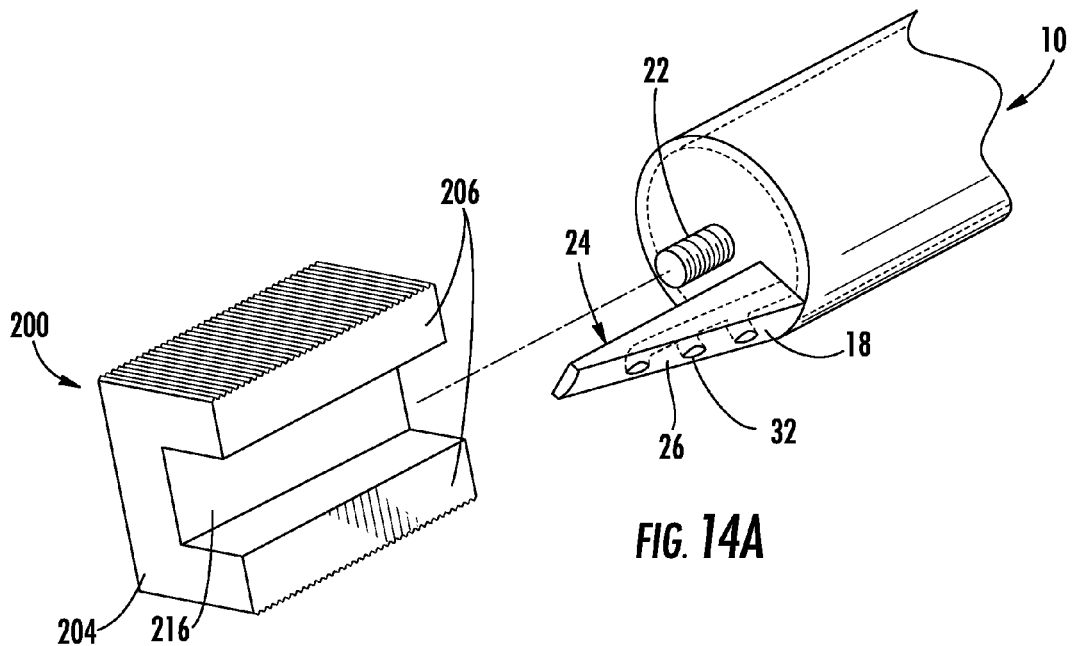
FIG. 14A is a perspective view of the intervertebral spacer of FIG. 13 prior to coupling to a distal end section of an insertion tool, according to an exemplary embodiment.
Figure 14B:
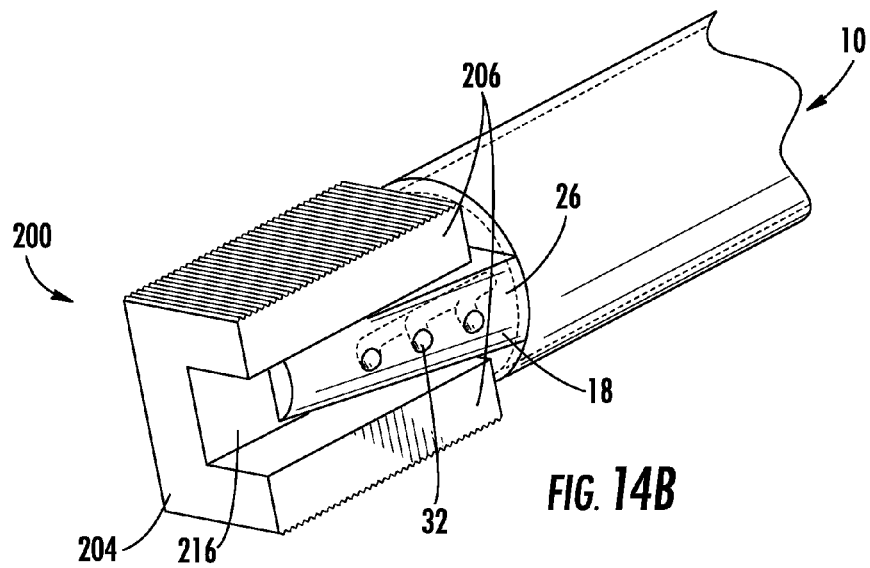
FIG. 14B is a perspective view of the intervertebral spacer of FIG. 13 coupled to the distal end section of an insertion tool, according to an exemplary embodiment.

Referring to FIG. 14A and FIG. 14B, engagement between tool 10 and spacer 200 is shown. In the embodiment shown, spacer 200 may be coupled to a tool 10 that includes a single arm 18 extending from the distal end. It should be noted that in FIG. 14A, tool 10 is shown rotated relative to spacer 200 so that threaded post 22 is visible. In this embodiment, spacer 200 is coupled to tool 10 primarily by threaded post 22 with arm 18 received by spacer 200 such that the inner surface 24 of arm 18 faces and is in contact with outer surface 216. In this embodiment, single arm 18 provides a fluid delivery path to the intervertebral space on one side of spacer 200. It should be understood that spacer 50, spacer 120, spacer 150 and spacer 200 are examples of differently shaped spacers that may be selected as needed for a particular procedure or for a particular patient.

Various components of the intervertebral insertion systems discussed herein may be made from a wide variety of suitable materials, including high strength biocompatible metals, plastics and ceramics. In exemplary embodiments, an insertion tool, such as insertion tool 10, may be made from a hard, substantially rigid, biocompatible material, such as surgical stainless steel alloys or high strength plastics. Spacers, such as spacers 50, 120, 150 and 200, may be constructed from a wide variety of rigid, noncompressible, biocompatible metals, such as alloys of cobalt and chromium (e.g., Vitallium), titanium alloys, stainless steel alloys, various surgical grade plastics and various absorbable biomaterials.

In other embodiments, insertion tool 10 may be used to insert various other structures in addition to the spacers discussed above. In one such embodiment, insertion tool 10 may be used to place allograft bone or cadaver bone into the intervertebral space. The allograft bone inserted using tool 10 may function as an insert to maintain distance between adjacent vertebrae during a fusion procedure. Following insertion of the allograft bone, various fluids may be delivered to the intervertebral space via tool 10 as discussed above.

Tool 10 may be used to deliver a wide variety of fluids to intervertebral space 90 during a surgical procedure. For example, the fluid may be a medicine, drug, or a fixation fluid, such as bone cement. The fluid may also be a fluid to promote bone growth during a spinal fixation procedure. Examples of fluids that may be delivered to intervertebral space 90 via tool 10 may include, among others, osteoconductive materials, osteoinductive materials, a slurry of biocompatible materials, resorbable culture mediums, tissue growth or differentiation factors (e.g., recombinant morphogenetic proteins, bone morphogenic proteins, PDGF, TGF-.beta., EGF/TGF-.alpha., IGF-I, .beta.FGF, BMP(x), etc.), hydrogels, resorbable or nonresorbable synthetic or natural polymers (collagen, fibrin, polyglycolic acid, polylactic acid, polytetrafluoroethylene, etc.), antibiotics, anti-inflammatory medications, immunosuppressive medications, anti-cancer drugs, and various other fluids, viscous fluids, pastes, or similar substances.

Figure 15:
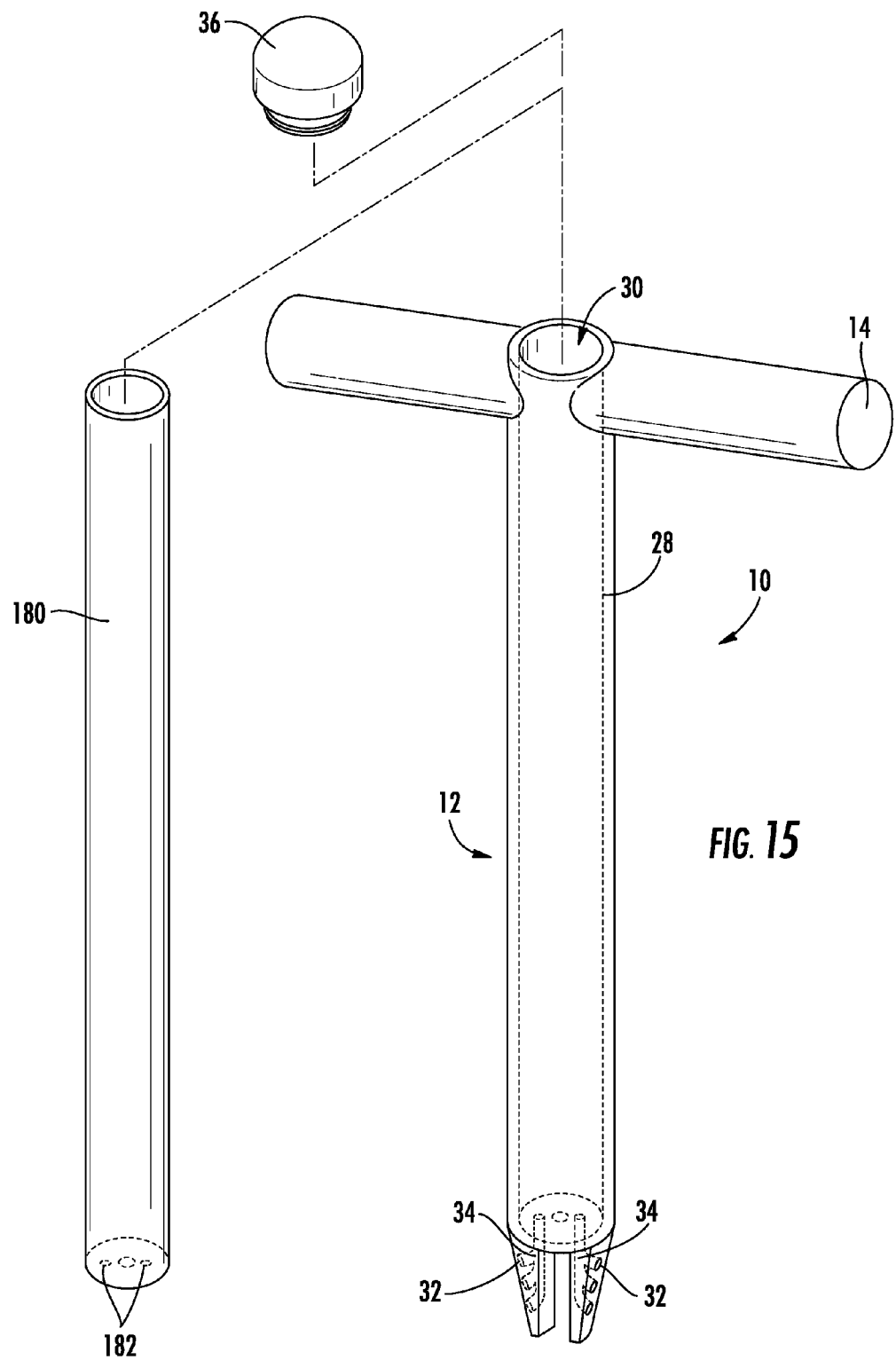
FIG. 15 is a perspective view of an insert for use with the insertion tool of FIG. 1, according to an exemplary embodiment.

Referring to FIG. 15, an intervertebral insert system including an insertion tool 10 and a liner or sleeve 180, is shown according to an exemplary embodiment. Generally, sleeve 180 may be used to protect cannulation 28 of tool 10 from the fluid injected through tool 10 and into the intervertebral space. As shown in FIG. 15, sleeve 180 may be received within cannulation 28 of tool 10 to provide a barrier between the fluid and the inner surface of cannulation 28. Sleeve 180 is a hollow tube and is generally shaped to match the shape of cannulation 28 and is sized to fit tightly along the inner surface of cannulation 28. Sleeve 180 includes one or more openings 182 configured to align with channels 34 associated with openings 32 of tool 10.

In this embodiment, sleeve 180 may be placed within cannulation 28 prior to coupling the fluid source to tool 10. Fluid is then delivered through the sleeve 180 and cannulation 28 to openings 32 in tool 10. Following a procedure, sleeve 180 is then removed from cannulation 28 and may be discarded. Most of the residual fluid left within tool 10 is removed along with sleeve 180, and consequently, sleeve 180 limits the amount of residual fluid that remains within cannulation 28 of tool 10 following use. Thus, sleeve 180 facilitates cleaning and reuse of tool 10 by limiting the amount of residual fluid that may be left within cannulation 28 following use. In one embodiment, sleeve 180 may be constructed from a rigid, inexpensive, disposable polymer material, and, in another embodiment, sleeve 180 may be constructed from a non-rigid, inexpensive, disposable polymer material.

In particular, sleeve 180 may be used when tool 10 is used to deliver a curable material, such as bone cement, and, in this application, residual bone cement may harden within sleeve 180. Following use, sleeve 180 may be removed from tool 10. Any bone cement that has hardened within sleeve 180 is removed along with sleeve 180 leaving cannulation 28 of tool 10 substantially free of hardened residual bone cement.

A variety of methods for implanting an insert into an intervertebral space and methods for delivering fluid into an intervertebral space using the devices disclosed herein are discussed below. In one embodiment, the method includes creating an opening in a patient, exposing a space between two vertebrae, and providing an insert and an insertion tool. In various embodiments, the insert may be spacer 50, spacer 120, spacer 150 or spacer 200 discussed above, and the tool may be tool 10 discussed above. In this method, the insert is coupled to the distal end of the tool, and the insert and the distal end of the tool are inserted into the intervertebral space. Fluid is then delivered from the proximal end of the tool, through the tool, and directly into the intervertebral space. During one such method fluid is not delivered into a hollow portion of the insert, and the insert does not include any portion that forms part of the fluid delivery path from the tool into the intervertebral space. In one embodiment of the method, the insert is inserted into the intervertebral space in a first orientation via manipulation of the tool, and the insert is rotated via the tool into a final position in which gripping surfaces engage the vertebrae adjacent to the space.

In another embodiment, the method includes creating an opening in a patient, exposing a space between two vertebrae, and providing an insert and an insertion tool. In various embodiments, the insert may be spacer 50, spacer 120, spacer 150 or spacer 200 discussed above, and the tool may be tool 10 discussed above. The insert is coupled to the distal end of the tool. The tool includes a tapered section at its distal end, and during insertion the outer surface of the tapered section engages the vertebral bodies adjacent the intervertebral space, such that the tool causes distraction of the adjacent vertebrae during insertion. In this method, the gradual slope of the tapered surface spreads the adjacent vertebrae apart as the user applies a force to the tool to move the tool further into the intervertebral space. The outer surface of the tapered section may be substantially smooth such that the tapered section of the insertion surfaces slides past the adjacent vertebrae. With the adjacent vertebrae distracted by the tapered section of the tool, the user then rotates the insert via rotation of the tool to bring gripping surfaces of the insert into engagement with the adjacent vertebrae. The separation between the adjacent vertebrae created by the tapered section of the tool provides the extra space needed to allow the insert to rotate into the final position with relative ease. Further, the circumferential curve of the outer surfaces of the tapered section facilitates the sliding of the outer surface of the tapered section past the adjacent vertebrae during rotation of the insert into the final position. After rotation, fluid may be delivered directly into the intervertebral space through the tool, and, in one embodiment, fluid is delivered directly into the intervertebral space through openings located along the tapered section of the tool. The tool may be decoupled from the insert and removed leaving the insert in place within the intervertebral space.

While the embodiments discussed herein relate primarily to an intervertebral insert system including an implant that is inserted into the intervertebral space in a first orientation and then rotated into a second orientation, in other embodiments, the implant does not need to be rotated into its final position. For example, the spacers discussed herein (e.g., spacer 50, spacer 120, spacer 150, etc.) may be inserted in an orientation in which the gripping surfaces of the spacer face the surfaces of the adjacent vertebrae, and thus, in this embodiment, no rotation is needed following insertion to bring the gripping surfaces into engagement with the adjacent vertebrae.

Further modifications and alternative embodiments of various aspects of the invention will be apparent to those skilled in the art in view of this description. Accordingly, this description is to be construed as illustrative only. The construction and arrangements, shown in the various exemplary embodiments, are illustrative only. While the current application recites particular combinations of features in the claims appended hereto, various embodiments of the invention relate to any combination of any of the features described herein whether or not such combination is currently claimed, and any such combination of features may be claimed in this or future applications. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Some elements shown as integrally formed may be constructed of multiple parts or elements, the position of elements may be reversed or otherwise varied, and the nature or number of discrete elements or positions may be altered or varied. The order or sequence of any process, logical algorithm, or method steps may be varied or re-sequenced according to alternative embodiments. Other substitutions, modifications, changes and omissions may also be made in the design, operating conditions and arrangement of the various exemplary embodiments without departing from the scope of the present invention.

What is claimed is:

1. A system for delivering fluid to a space between two vertebrae comprising:
   an insert configured to be implanted in the space between two vertebrae; and
   a tool comprising:
      a proximal end;
      a distal end;
      a structure at the distal end configured to be coupled to the insert, wherein the structure comprises a first arm and a second arm, the first arm and the second arm each including an inner surface and an outer surface;
      a first opening located near the proximal end of the tool;
      a second opening located near the distal end of the tool, wherein the second opening is located along the outer surface of the first arm near the distal end of the tool; and
      a passage extending between the first opening and the second opening, the first opening, the passage and the second opening providing a fluid delivery path from the proximal end to the exterior of the tool near the distal end;
   wherein the second opening is positioned relative to the structure such that when the insert is coupled to the structure at the distal end of the tool, fluid is permitted to be delivered through the passage and from the tool directly into the space between the two vertebrae without requiring fluid to be delivered through the insert.

2. The system of claim 1, further comprising a third opening located along the outer surface of the second arm, wherein the first opening, the passage and the third opening provide a fluid delivery path from the proximal end to the outer surface of the second arm to permit delivery of fluid from to the tool directly into the space between the two vertebrae.

3. The system of claim 1, wherein the insert includes an outer surface, wherein, when the insert is placed between the first arm and the second arm, the inner surfaces of the first arm and the second arm engage the outer surface of the insert to couple the insert to the tool.

4. The system of claim 3, wherein the inner surfaces of the first arm and the second arm engage opposite sides of the outer surface of the insert.

5. The system of claim 1, wherein the insert further comprises:
   a pair of opposing substantially smooth insertion surfaces, the pair of insertion surfaces configured to slidably engage vertebral bone material during insertion of the insert into the space between two vertebrae; and
   a pair of opposing gripping surfaces configured to grip vertebral bone material;
   a pair of opposing outer surfaces substantially parallel to the pair of opposing insertion surfaces;
   wherein the inner surfaces of the first arm and the second arm each engage one of the pair of opposing outer surfaces to couple the insert to the tool.

6. The system of claim 5, further comprising a third opening located along the outer surface of the second arm, wherein the first opening, the passage and the third opening provide a fluid delivery path from the proximal end to the outer surface of the second arm such that fluid can be delivered from the tool directly into the space between the two vertebrae on opposite sides of the insert.

7. The system of claim 5, wherein the pair of insertion surfaces are substantially perpendicular to the pair of gripping surfaces.

8. The system of claim 5, wherein the insert is substantially "I" shaped and is formed from a solid, single piece of material.

9. The system of claim 1, wherein the outer surfaces of the first and second arms are tapered such that the distance between the outer surfaces decreases as the distance from the proximal end increases, the taper providing distraction of adjacent vertebrae during insertion of the insert.

10. The system of claim 1, further comprising a hollow sleeve inserted within at least a portion of the passage to provide a barrier between the fluid and the material of the tool.

11. An intervertebral insert system comprising:
   an insert configured to be implanted into an intervertebral space, the insert including an outer surface; and
   a tool comprising:
      a proximal end;
      a distal end having an inner surface and an outer surface, the distal end coupled to the insert, wherein the inner surface faces the outer surface of the insert and the outer surface is configured to face the intervertebral space;
      a first opening located near the proximal end;
      a second opening located along the outer surface of the distal end; and
      a passage extending between the first opening and the second opening to provide a fluid delivery path from the proximal end to the exterior of the tool through the second opening without requiring fluid to be delivered through the insert when the insert is coupled to the distal end of the tool; and wherein the insert further comprises a proximal face and an aperture located along the proximal face, wherein the tool further comprises a post located at the distal end, wherein the post of the tool is received within the aperture of the insert to couple the insert to the tool.

12. The system of claim 11, wherein the distal end comprises a first arm and a second arm, each arm including an inner surface and an outer surface.

13. The system of claim 12, further comprising a third opening, wherein the second opening is located along the outer surface of the first arm and the third opening is located is along the outer surface of the second arm, wherein the passage extends between the first opening and the third opening to provide a fluid delivery path from the proximal end to the exterior of the tool through the third opening.

14. The system of claim 12, wherein the insert is located between the first arm and the second arm and the inner surfaces of the first arm and the second arm engage the outer surface of the insert to couple the insert to the tool.

15. The system of claim 11, wherein the aperture is threaded and the post includes threads, such that the post may be threaded into the aperture.

* * * * *